United States Patent [19]

Baumann et al.

[11] Patent Number: 5,362,872
[45] Date of Patent: Nov. 8, 1994

[54] CHROMOGENIC LACTAMS

[75] Inventors: Hans Baumann, Oberwil; Rox Phaff, Itingen, both of Switzerland

[73] Assignee: Ciba-Geigy Corporation, Ardsley, N.Y.

[21] Appl. No.: 28,899

[22] Filed: Mar. 10, 1993

[30] Foreign Application Priority Data

Mar. 13, 1992 [CH] Switzerland ............... 815/92

[51] Int. Cl.$^5$ .......................... C07D 265/12
[52] U.S. Cl. ........................ 544/89; 544/95; 544/54
[58] Field of Search ............... 544/90, 89, 95

[56] References Cited

U.S. PATENT DOCUMENTS 3,509,147  4/1970  Houlihan ............ 260/251

FOREIGN PATENT DOCUMENTS

| | | |
|---|---|---|
| 181283 | 5/1986 | European Pat. Off. |
| 475908 | 3/1992 | European Pat. Off. |
| 0560722 | 9/1993 | European Pat. Off. |
| 1251348 | 10/1967 | Germany |
| 2242250 | 1/1974 | Germany |
| 989264 | 4/1965 | United Kingdom |
| 1156725 | 7/1969 | United Kingdom |
| 1301052 | 12/1972 | United Kingdom |
| 1355124 | 5/1974 | United Kingdom |

OTHER PUBLICATIONS

Chemical Abstracts vol. 120 54549(a) 1993.
Journal of the Chemical Society 1965 Abramowitz et al. pp. 2165–2173.

*Primary Examiner*—Nicholas Rizzo
*Attorney, Agent, or Firm*—George R. Dohmann

[57] ABSTRACT

The invention relates to chromogenic lactams, to their preparation and to the use thereof in pressure-sensitive or heat-sensitive recording materials.

The novel lactams have the general formula I

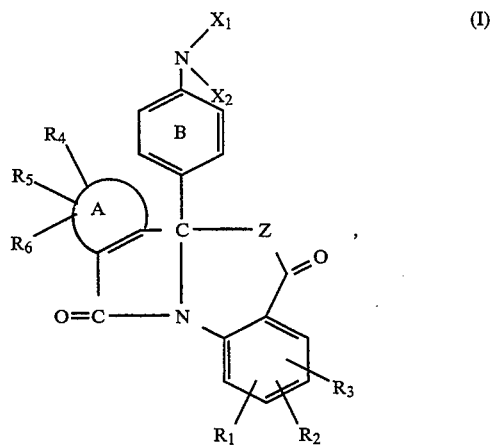

wherein the ring A is an aromatic or heteroaromatic radical containing 6 ring atoms;

the ring B is an unsubstituted or substituted benzene nucleus; and

Z is $$-\underset{|}{N}R, \text{ or } O;$$

$R$, $R_1$, $R_2$, $R_3$, $R_4$, $R_5$, $R_6$, $X_1$ and $X_2$ are as defined in the description.

13 Claims, No Drawings

CHROMOGENIC LACTAMS

The present invention relates to chromogenic lactams, to their preparation and to the use thereof in pressure-sensitive or heat-sensitive recording materials.

The novel lactams have the general formula I

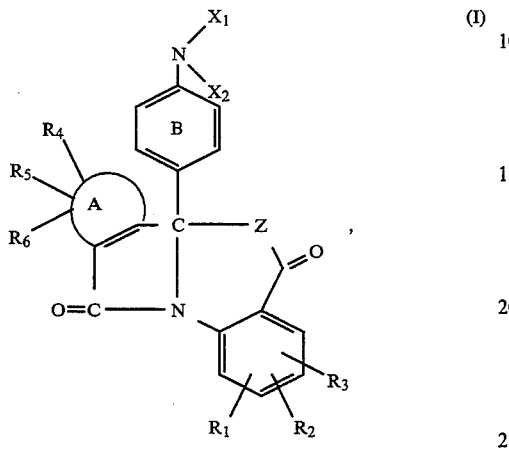

wherein
the ring A is an aromatic or heteroaromatic radical which contains 6 ring atoms and may contain an aromatic fused ring;
the ring B is a benzene nucleus which may be substituted by halogen, lower alkyl, lower alkoxy, benzyloxy, or lower alkylcarbonylamino, mono- or di-lower alkylamino;
Z is

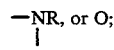

R is hydrogen; lower alkyl which is unsubstituted or substituted by halogen, hydroxy, cyano, benzoyl, acyl, di-lower alkylamino or lower alkoxy; cycloalkyl of 5 to 10 carbon atoms; aryl or aralkyl which are each unsubstituted or ring-substituted by halogen, cyano, nitro, $C_1$–$C_4$haloalkyl, lower alkyl, lower alkoxy, lower alkoxycarbonyl or acyl; acyl; N-lower alkylcarbamoyl; or unsubstituted or ring-substituted N-arylcarbamoyl;
$R_1$, $R_2$ and $R_3$ are each independently of one another hydrogen; lower alkyl; lower alkoxy; lower alkylthio; lower alkylsulfonyl; sulfo; hydroxy; nitro; halogen; amino; mono-lower alkylamino; di-lower alkylamino; arylamino; aryl-lower alkylamino; diarylamino; aralkylamino; aralkyl-lower alkylamino; diaralkylamino; or a wholly or partially saturated heterocyclic radical which is attached at a ring nitrogen atom;
$R_2$ and $R_3$ together are an unsubstituted or a lower alkyl-substituted, vicinally linked methylenedioxy or 1,2-ethylene dioxy group;
$R_4$, $R_5$ and $R_6$ are each independently of one another hydrogen; halogen; cyano; nitro; lower alkyl; lower alkylthio; lower alkylcarbonyl; lower alkoxycarbonyl; amino; mono-lower alkylamino; di-lower alkylamino; arylamino; aryl-lower alkylamino; diarylamino; aralkylamino; aralkyl-lower alkylamino; diaralkylamino; cycloalkylamino; dicycloalkylamino; lower alkyl-cycloalkylamino; lower alkoxy; lower alkylthio; lower alkylsulfonyl; or a wholly or partially saturated heterocyclic radical which is attached at a ring nitrogen atom;
$X_1$ and $X_2$ are each independently of the other hydrogen; alkyl of not more than 12 carbon atoms which is unsubstituted or substituted by halogen, hydroxy, cyano, tetrahydrofuryl or lower alkoxy; acyl of 1 to 8 carbon atoms; cycloalkyl of 5 to 10 carbon atoms; or aralkyl or aryl which are each unsubstituted or ring-substituted by halogen, cyano, nitro, trifluoromethyl, lower alkyl, lower alkoxy, lower alkoxycarbonyl, —NX'X" or 4-X'X"N-phenylamino, wherein X' and X" are each independently of the other hydrogen, lower alkyl, cyclohexyl, benzyl or phenyl; or
$X_1$ and $X_2$ together with the linking nitrogen atom are a 5- or 6-membered, preferably saturated, heterocyclic radical.

A as a 6-membered aromatic ring is preferably a benzene ring, and as a 6-membered heterocyclic ring is preferably a nitrogen-containing heterocycle having aromaticity, typically a pyridine or pyrazine ring. The ring A may also contain a fused aromatic ring, preferably a benzene ring, and is hence a naphthalene, quinoline or quinoxaline ring.

A preferred 6-membered aromatic or heterocyclic radical A is a 2,3-pyridino, 3,4-pyridino, 2,3-pyrazino, 2,3-quinoxalino, 1,2-naphthalino, 2,3-naphthalino or 1,2-benzo radical.

In addition to carrying the mandatory substituent —$NX_1X_2$, the ring B is preferably unsubstituted or polysubstituted by halogen, lower alkyl, lower alkoxy, acetylamino mono-lower alkylamino or di-lower alkylamino. The ring B is most preferably an unsubstituted or a lower alkoxy-substituted phenyl radical.

Preferably the substituent R in the group Z defined

is hydrogen, lower alkyl, cyano-lower alkyl, lower alkylcarbonyl such as acetyl, phenyl, benzyl, N-lower alkylcarbamoyl or N-phenylcarbamoyl (carbanilino) which is unsubstituted or substituted by halogen, nitro, trifluoromethyl, lower alkyl, lower alkoxy or lower alkoxycarbonyl. Preferably Z is

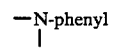

or, most preferably,

Alkyl groups in formula I are preferably straight-chain or branched and contain up to 12 carbon atoms in the chain. Typical examples of such alkyl groups are methyl, ethyl, n-propyl, isopropyl, n-butyl, 1-methylbutyl, sec-butyl, ten-butyl, amyl, isoamyl, n-hexyl, 2-ethylhexyl, n-heptyl, n-octyl, isooctyl, 1,1,3,3-tetramethylbutyl, n-nonyl, isononyl, 3-ethylheptyl, decyl or n-dodecyl.

Substituted alkyl groups in formula I are preferably cyanoalkyl, haloalkyl, hydroxyalkyl or lower alkoxyalkyl, each preferably containing a total of 2 to 8 carbon atoms. Exemplary of such groups are 2-cyanoethyl, 2-chloroethyl, 2-chloropropyl, 2-hydroxyethyl, 3-hydroxypropyl, 2-methoxyethyl, 2-ethoxyethyl, 2,3-dihydroxypropyl, 2-hydroxy-2-chloropropyl, 3-methoxypropyl, 4-methoxybutyl, trichloromethyl, trifluoromethyl, tetrafluoroethyl, tetrachloroethyl or 4-propoxybutyl, and are also tetrahydrofurfuryl in the definition of $X_1$ and $X_2$.

Cycloalkyl may typically be cyclopentyl, cycloheptyl or, preferably, cyclohexyl. The cycloalkyl radicals may contain one or more than one $C_1$-$C_4$alkyl, preferably methyl, group, and contain a total of 5 to 10 carbon atoms.

Aralkyl is preferably phenyl-$C_1$-$C_4$alkyl, typically phenethyl, phenylisopropyl or, most preferably, benzyl. Aryl substituents in formula I are preferably naphthyl or, most preferably, phenyl.

Preferred substituents of the aralkyl and aryl moiety of the radicals X are typically halogen, cyano, $C_1$-$C_4$alkyl, $C_1$-$C_4$haloalkyl, $C_1$-$C_4$alkoxy, e.g. methyl, trifluoromethyl, methoxy or carbomethoxy. Preferred substituents of the aryl radical R are typically halogen, methyl or methoxy. Exemplary of such araliphatic and aromatic radicals are methylbenzyl, 2,4- or 2,5-dimethylbenzyl, chlorobenzyl, dichlorobenzyl, cyanobenzyl, tolyl, xylyl, chlorophenyl, methoxyphenyl, trifluoromethylphenyl, 2,6-dimethylphenyl or carbomethoxyphenyl.

A heterocyclic radical —$NX_1X_2$ or a substituent $R_1$ to $R_6$ as a wholly or partially saturated heterocycle which is attached at a ring nitrogen atom may be pyrrolidino, piperidino, pipecolino, morpholino, thiomorpholino or piperazino, typically N-methylpiperazino or N-phenylpiperazino. Preferred saturated heterocyclic radicals are pyrrolidino, piperidino or morpholino.

The substituents $X_1$ and $X_2$ are preferably cyclohexyl, tolyl, benzyl, phenyl, cyano-lower alkyl, e.g. 2-cyanoethyl or, most preferably, lower alkyl such as methyl, ethyl, n-propyl, isopropyl, n-butyl or isoamyl.—$NX_1X_2$ is preferably also pyrrolidino, N-lower alkyl-N-tetrahydrofurfurylamino, 4-di-lower alkylaminophenylamino or 4-(4'-phenylarninophenylamino)phenylamino.

Lower alkyl, lower alkoxy and lower alkylthio are preferably those groups or moieties which contain 1 to 6, preferably 1 to 4, carbon atoms. Typical examples of such groups are methyl, ethyl, n-propyl, isopropyl, n-butyl, sec-butyl, amyl, isoamyl or hexyl; methoxy, ethoxy, isopropoxy, isobutoxy, tert-butoxy or amyloxy; and methylthio, ethylthio, propylthio or butylthio.

Halogen is typically fluoro, bromo, iodo or, preferably, chloro. "Acyl" is preferably formyl, lower alkylcarbonyl such as acetyl or propionyl, or benzoyl. Further acyl radicals may be lower alkylsulfonyl such as methylsulfonyl or ethylsulfonyl, lower alkoxysulfonyl such as methoxysulfonyl or ethoxysulfonyl, as well as phenylsulfonyl or phenoxysulfonyl. Benzoyl and phenylsulfonyl may be substituted by halogen, methyl, methoxy or ethoxy.

Preferred compounds are compounds of formula I

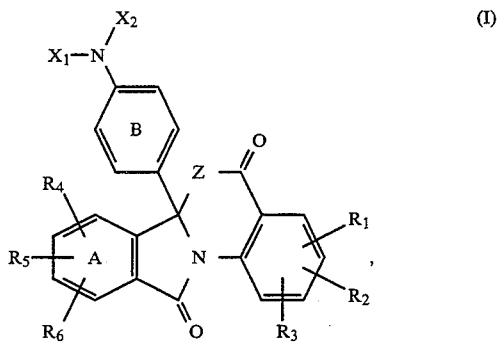

wherein
the ring B is a benzene nucleus which may be substituted by halogen, lower alkyl, lower alkoxy or benzyloxy;
Z is

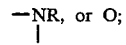

R is hydrogen; lower alkyl which is unsubstituted or substituted by halogen or lower alkoxy; cycloalkyl of 5 to 10 carbon atoms; phenyl or benzyl which are each unsubstituted or ting-substituted by halogen, cyano, nitro, $C_1$-$C_4$haloalkyl, lower alkyl or lower alkoxy; acyl;
$R_1$, $R_2$ and $R_3$ are each independently of one another hydrogen; lower alkyl; lower alkoxy; lower alkylthio; lower alkylsulfonyl; sulfo; hydroxy; nitro; halogen; amino; mono-lower alkylamino; di-lower alkylamino; arylamino; aryl-lower alkylamino; diarylamino; aralkylamino; aralkyl-lower alkylamino; diaralkylamino; or a wholly or partially saturated heterocyclic radical which is attached at a ring nitrogen atom;
$R_2$ and $R_3$ together are an unsubstituted or a lower alkyl-substituted, vicinally linked methylenedioxy group or 1,2-ethylene dioxy group;
$R_4$, $R_5$ and $R_6$ are each independently of one another hydrogen; halogen; cyano; nitro; lower alkyl; lower alkylthio; lower alkylcarbonyl; lower alkoxycarbonyl; amino; mono-lower alkylamino; all-lower alkylamino; arylamino; aryl-lower alkylamino; diarylamino; aralkylamino; aralkyl-lower alkylamino; diaralkylamino; cycloalkylamino; dicycloalkylamino; lower alkyl-cycloalkylamino; lower alkoxy; lower alkylthio; lower alkylsulfonyl; or a wholly or partially saturated heterocyclic radical which is attached at a ring nitrogen atom;
$X_1$ and $X_2$ are each independently of the other hydrogen; alkyl of not more than 12 carbon atoms which is unsubstituted or substituted by halogen, hydroxy, cyano, tetrahydrofuryl or lower alkoxy; acyl of 1 to 8 carbon atoms; cycloalkyl of 5 to 10 carbon atoms; or aralkyl or aryl which are each unsubstituted or ting-substituted by halogen, cyano, nitro, trifiuoromethyl, lower alkyl or lower alkoxy; or
$X_1$ and $X_2$ together with the linking nitrogen atom are a 5- or 6-membered, preferably saturated, heterocyclic radical.

Particularly preferred compounds are compounds of formula I

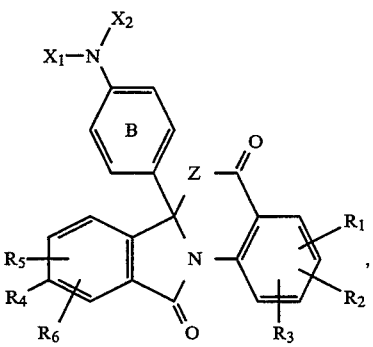

(I)

wherein
the ring B is a benzene nucleus which is unsubstituted or substituted by halogen or lower alkyl;
Z is

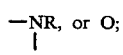

−NR, or O;

R is hydrogen;
$R_1$ is hydrogen; $C_1$–$C_4$alkyl; $C_1$–$C_4$alkoxy; sulfo; nitro; halogen; mono-$C_1$–$C_4$alkylamino; di-$C_1$–$C_4$alkylamino; phenylamino; phenyl-$C_1$–$C_4$alkylamino; diphenylamino; benzylamino; benzyl-$C_1$–$C_4$alkylamino; dibenzylamino;
$R_2$ and $R_3$ are each independently of the other hydrogen, $C_1$–$C_4$alkyl; or halogen;
$R_2$ and $R_3$ together are a vicinally linked methylenedioxy or 1,2-ethylene dioxy group;
$R_4$ is hydrogen; amino; mono-$C_1$–$C_4$alkylamino; di-$C_1$–$C_4$alkylamino; phenylamino; phenyl-$C_1$–$C_4$alkylamino; diphenylamino; benzylamino; benzyl-$C_1$–$C_4$alkylamino; dibenzylamino; cycloalkylamino; dicycloalkylamino; or $C_1$–$C_4$alkylcycloalkylamino;
$R_5$ and $R_6$ are each independently of the other hydrogen; halogen; cyano; nitro; $C_1$–$C_4$alkyl; $C_1$–$C_4$alkylthio; or $C_1$–$C_4$alkoxy;
$X_1$ and $X_2$ are each independently of the other hydrogen; unsubstituted or $C_1$–$C_4$alkoxy-substituted alkyl of not more than 12 carbon atoms; cyclohexyl; benzyl or phenyl which are each unsubstituted or ring-substituted by halogen, $C_1$–$C_4$alkyl or $C_1$–$C_4$alkoxy; or
$X_1$ and $X_2$ together with the linking nitrogen atom are a 5- or 6-membered, preferably saturated, heterocyclic radical.

Among the compounds of formula I and the preferred and particularly preferred compounds of formula I, the following groups a) to g) are of particular interest:
a) Compounds of formula I, wherein
   Z is O;
b) compounds of formula I, wherein
   $R_1$ is as previously defined,
   $R_2$ is hydrogen, halogen or $C_1$–$C_4$alkyl and
   $R_3$ is halogen or hydrogen;
c) compounds of formula I, wherein
   $R_1$ is mono-$C_1$–$C_4$alkylamino; di-$C_1$–$C_4$alkylamino;
   $R_2$ hydrogen or $C_1$–$C_4$alkyl, and
   $R_3$ is hydrogen;
d) compounds of formula I, wherein
   $R_4$ is $C_1$–$C_4$alkoxy; mono-$C_1$–$C_4$alkylamino; di-$C_1$–$C_4$alkylamino; phenylamino; phenyl-$C_1$–$C_4$alkylamino; diphenylamino; benzylamino; benzyl-$C_1$–$C_4$alkylamino; dibenzylamino; cycloalkylamino; dicycloalkylamino; or $C_1$–$C_4$alkylcycloalkylamino;
e) compounds of formula I, wherein
   $R_4$ is mono-$C_1$–$C_4$alkylamino, di-$C_1$–$C_4$alkylamino, phenylamino, phenyl-$C_1$–$C_4$alkylamino, diphenylamino, benzylamino, benzyl-$C_1$–$C_4$alkylamino, dibenzylamino;
f) compounds of formula I, wherein
   $X_1$ and $X_2$ are each independently of the other hydrogen, unsubstituted alkyl of not more than 6 carbon atoms, benzyl or phenyl;
g) compounds of formula I, wherein
   $X_1$ and $X_2$ are each independently of the other unsubstituted alkyl of not more than 6 carbon atoms, benzyl or phenyl.

The lactams of formula (I) are novel compounds. They can be prepared by methods which are known per se.

The novel lactams are conveniently prepared by reacting a ketonic acid of formula

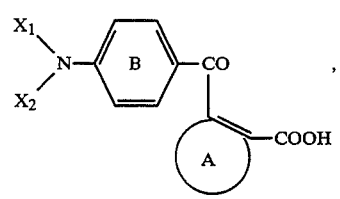

(II)

wherein $X_1$, $X_2$, A and B are as previously defined, with a bifunctional amino compound of formula

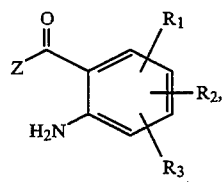

(III)

wherein $R_1$, $R_2$, $R_3$ and Z are as previously defined.

The reaction is preferably carried out in an inert organic solvent at elevated temperature, preferably at up to boiling temperature.

Suitable organic solvents which form the reaction medium are cycloaliphatic or, preferably, aromatic hydrocarbons, typically cyclohexane, benzene; toluene or xylene; chlorinated hydrocarbons such as ethylene chloride, tetrachloroethylene or chlorobenzenes such as chlorobenzene, chlorotoluene or dichlorobenzene; cyclic ethers such as dioxane or tetrahydrofuran; dimethyl sulfoxide or nitriles of aliphatic monocarboxylic acids such as acetonitrile, propionitrile or butyronitrile. It is also possible to use mixtures of the cited solvents. Preferred solvents are chlorobenzene, chlorotoluene and, most preferably, toluene.

The final product is isolated in conventional known manner by separating the aqueous phase and removing the solvent, or by treatment with a suitable organic solvent such as methanol, isopropanol or petroleum ether.

Depending on the meaning of Z, the bifunctional compounds of formula (III) may be anthranilic acid, an anthranilamide, aminonaphthoic acid or an aminonaphthamide.

Amino compounds of formula (III) which may suitably be used for reaction with the ketonic acids of formula (II) are aminonaphthoic acid, 4-nitroanthranilic acid, 3,5-diiodoanthranilic acid, 3-hydroxyanthranilic, 3-methylanthranilic, 4-chloroanthranilic acid, 6-methylanthranilic acid, 5-bromoanthranilic, 5-chloroanthranilic, 5-iodoanthranilic acid, 5-hydroxyanthranilic acid, 5-methylanthranilic, 4,5-dimethylanthranilic acid, 5-methoxyanthranilic acid, 5-nitroanthranilic acid, 3,5-dichloroanthranilic acid, 3,5-dimethylanthranilic acid, 3,4-methylenedioxyanthranilic acid, 3-nitroanthranilic acid, 3-sulfoanthranilic acid, 3,4,5-trimethoxyanthranilic acid, or 5-fluoroanthranilic acid.

Compounds of formula (I), wherein Z is

and R is acyl, N-lower alkylcarbamoyl or unsubstituted or substituted N-phenylcarbamoyl, can also be prepared by reacting a lactam of formula (I), wherein Z is

in conventional manner with a reactive functional derivative of a carboxylic acid or sulfonic acid, preferably halides or anhydrides, typically acetic anhydride, acetyl chloride, acetyl bromide, benzoyl chloride, benzenesulfonyl chloride, or also with isocyanates such as lower alkylisocyanates, phenyl isocyanate, halophenyl isocyanate or lower alkylphenyl isocyanate.

The lactams of formula (I) are normally colourless or at most faintly coloured. When these colour formers are brought into contact preferably with an acid developer, i.e. an electron acceptor, then, depending on the meaning of Z and the developer, they produce deep yellow, red, violet, greenish blue, blue or green images which are fast to sublimation and light. The lactams of formula (I) are also very useful in admixture with one or more other known colour formers, typically 3,3-(bisaminophenyl)phthalides such as CVL, 3-indolyl-3-aminophenylaza- or -diazaphthalides, (3,3-bisindolyl)phthalides, 3-aminofluorans, 2,6-diaminofluorans, 2,6-diamino-3-methylfluorans, 3,6-bisalkoxyfluorans, 3,6-bisdiarylaminofluorans, leukoauramines, spiropyranes, spirodipyranes, chromenopyrazoles, chromenoindoles, phenoxazines, phenothiazines, quinazolines, rhodamine lactams, carbazolyl methanes or other triarylmethaneleuko colorants to give navy blue, grey or black images.

The lactams of formula (I) exhibit an excellent colour intensity and lightfastness on activated clays as well as on phenolic substrates. They are particularly suitable for use as colour formers in a heat-sensitive or, preferably, a pressure-sensitive recording material which may also be a copying material. They are pH-stable and have excellent solubility in the capsule oils. After exposure on a CB sheet they exhibit an insignificant decrease in colour strength (CB decline).

A pressure-sensitive material typically comprises at last one pair of sheets that contain at least one colour former of formula (I) dissolved in an organic solvent, and an electron acceptor as developer.

Typical examples of such developers are active clays such as attapulgite clay, acid clay, bentonite, montmorillonite, activated clay such as acid-activated bentonite or montmorillonite, and also zeolith, halloysite, silica, alumina, aluminium sulfate, aluminium phosphate, zinc chloride, zinc nitrate, zirconium dioxide, activated kaolin or any clay. As developers it is also possible to use acidic organic compounds such as not substituted or ring-substituted phenols, resorcinols, salicylic acids, including 3,5-bis($\alpha,\alpha$-dimethylbenzyl)salicylic acid or 3,5-bis($\alpha$-methylbenzyl)salicylic acid or salicylates and their metal salts, e.g. zinc salts, as well as an acidic polymeric material such as a phenolic polymer, an alkyl phenol acetylene resin, a maleic acid rosin resin or a partially or completely hydrolysed polymer of maleic anhydride with styrene, ethylene or vinyl methyl ether, or carboxymethylene. Mixtures of the cited monomers and polymers can also be used. Particularly preferred developers are acid-activated bentonite, zinc salicylates such as zinc 3,5-bis-$\alpha$-methylbenzylsalicylate or the condensates of p-substituted phenols with formaldehyde. These last mentioned compounds may also be modified with zinc. Zinc salicylates are disclosed, inter alia, in EP,A-181 283 or DE-A-2 242 250.

The developers may also be used in admixture with other basically inert or substantially inert pigments or with other auxiliaries such as silica gel or UV absorbers, e.g. 2-(2-hydroxyphenyl)benzotriazoles or 2-hydroxyphenyl-1,2,3-triazines. Examples of such pigments are: talcum, titanium dioxide, alumina, aluminium hydroxide, zinc oxide, chalk, clays such as kaolin, as well as organic pigments, e.g. urea/formaldehyde condensates (BET surface area: 2–75 m$^2$/g) or melamine/formaldehyde condensates.

The colour former produces a coloured mark at those points where it comes into contact with the electron acceptor. To prevent the colour formers contained in the pressure-sensitive recording material from becoming active prematurely, they are usually separated from the electron acceptor. This separation can conveniently be accomplished by incorporating the colour formers in foam-like, sponge-like or honeycomb-like structures. The colour formers are preferably encapsulated in microcapsules, which can normally be ruptured by pressure.

When the capsules are ruptured by pressure, for example with a pencil, the colour former solution is transferred to an adjacent sheet which is coated with an electron acceptor and a coloured image is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a halogenated paraffin, benzene or diphenyl, for example chloroparaffin, trichlorobenzene, monochlorodiphenyl or trichlorodiphenyl, and also esters such as tricresyl phosphate, di-n-butyl phthalate, dioctyl phthalate, trichloroethylphosphate, an aromatic ether such as benzylphenyl ether, hydrocarbon oils such as paraffin or kerosene, aromatic hydrocarbons, an alkylated derivative (e.g. containing isopropyl, isobutyl, sec- or tert-butyl groups) of diphenyl, naphthalene or terphenyl; dibenzyl toluene, partially hydrogenated terphenyl, mono- to tetra-C$_1$-C$_3$alkylated diphenylalkanes, dodecylbenzene, benzylated xylenes, phenyl xylyl ethane or other chlorinated or hydrogenated condensed aromatic hydrocarbons. Mixtures of different solvents, especially mixtures of paraffin oils or kerosene and diisopropylnaphthalene or partially hydrogenated terphenyl, are often used to obtain optimum solubility for the colour formation, a rapid and intense coloration, and a viscosity which is advantageous for the microencapsulation. For the encapsulation, the novel lactams are distinguished by the feature that they are readily soluble and are pH-resistant in a pH range from 4 to 10.

The capsule walls can be formed evenly around the droplets of the colour former solution by coacervation. The encapsulating material is described e.g. in U.S. Pat. No. 2,800,457. The capsules can also be formed conveniently from an aminoplast or a modified aminoplast by polycondensation, as described in British patent specifications 989 264, 1 156 725, 1 301 052, 4 100 103 and 1 355 124. Also suitable are microcapsules which are formed by interfacial polymerisation, e.g. capsules formed from polyester, polycarbonate, polysulfonamide, polysulfonate, but preferably from polyamide, polyurea or polyurethane.

The microcapsules containing the colour formers of formula (I) can be used for the production of a wide variety of known kinds of pressure-sensitive copying material. The various systems differ substantially from one another in the arrangement of the capsules, of the colour reactants, and of the support.

A preferred arrangement is that in which the encapsulated colour former is in the form of a layer on the back of a transfer sheet and the electron acceptor (colour developer) is in the form of a layer on the face of a receiver sheet. Another arrangement of the components is that wherein the microcapsules which contain the colour former, and the developer, are in or on the same sheet in the form of one or more individual layers, or the developer is incorporated in the support.

The capsules are preferably secured to the support by means of a suitable binder. As paper is the preferred support, these binders are principally paper-coating agents such as gum arabic, polyvinyl alcohol, hydroxymethyl cellulose, casein, methyl cellulose, dextrin, starch or starch derivatives or polymer latices. These latter are typically butadiene/styrene copolymers or acrylic homopolymers or copolymers.

The paper employed comprises not only normal paper made from cellulose fibres, but also paper in which the cellulose fibres are replaced (partially or completely) by synthetic polymers.

The copying paper preferably comprises a capsule-free layer that contains the colour former and a colour developing layer wherein the colour developer contains at least one inorganic metal salt of a polyvalent metal, preferably a halide or nitrate such as zinc chloride, zinc nitrate or a mixture thereof.

The compounds of formula (I) may also be used as colour formers in a thermoreactive recording material. This recording material usually comprises at least one support, one or more than one colour former, one electron acceptor, and optionally also a binder and/or wax. If desired, the recording material may also comprise an activator or sensitiser, e.g. benzyl diphenyl.

Thermoreactive recording systems comprise, for example, heat-sensitive recording or copying materials and papers. These systems are used e.g. for recording information, for example in electronic computers, teleprinters or telewriters, or in recording and measuring instruments, e.g. electrocardiographs. The image formation (marking) can also be effected manually with a heated pen. Laser beams can also be used to produce heat-induced images.

The thermoreactive recording material can be composed such that the colour former is dispersed or dissolved in one binder layer and the developer is dissolved or dispersed in the binder in a second layer. Another possibility comprises dispersing both the colour former and the developer in one layer. he layer or layers are softened by means of heat at specific areas and the desired colour develops at once at those areas where heat is applied.

Suitable developers are the same electron acceptors as are used in pressure-sensitive papers. Examples of developers are the clays and phenolic resins already mentioned, or also the phenolic compounds disclosed e.g. in German Offenlegungsschrift 1 25 1 348, for example 4-tert-butylphenol, 4-phenylphenol, methylene bis(p-phenylphenol), 4-hydroxydiphenyl ether, $\alpha$-naphthol, $\beta$-naphthol, 4-hydroxydiphenylsulfone, 4-hydroxy-4'-methyldiphenylsulfone, methyl or benzyl 4-hydroxybenzoate, 4'-hydroxy-4-isopropoxydiphenylsulfone, 4,4'-cyclohexylidenediphenol, 4,4'-isopropylidenediphenol, 4,4'-isopropylidene-bis(2-methylphenol), an antipyrine complex of zinc thiocyanate, a pyridine complex of zinc thiocyanate, 4,4-bis(4'-hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

It is preferred to use fusible, film-forming binders for the preparation of the thermoreactive recording material. These binders are normally water-soluble, whereas the lactams and the developer are sparingly soluble or insoluble in water. The binder should be able to disperse and fix the colour former and the developer at room temperature.

When heated, the binder softens or melts, so that the colour former comes in contact with the developer and a colour is able to form. Examples of binders which are soluble, or at least swellable, in water are hydrophilic polymers such as polyvinyl alcohol, polyacrylic acid, hydroxyethyl cellulose, methyl cellulose, carboxymethyl cellulose, polyacrylamide, polyvinyl pyrrolidone, gelatin, starch or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former and the developer are contained in one layer in a water-soluble binder.

To ensure the stability of the heat-sensitive recording material or the density of the developed image, the material may be provided with an additional protective layer. Such a protective layer will normally consist of water-soluble and/or water-insoluble resins which are conventional polymeric materials or aqueous emulsions of these polymeric materials.

The thermoreactive layers and resin coatings may contain further auxiliaries. To improve the degree of whiteness, to facilitate the printing of papers, and to prevent the heated pen from sticking, these layers may contain e.g. talcum, titanium dioxide, zinc oxide, alumina, aluminium hydroxide, calcium carbonate (e.g. chalk), clays or also organic pigments, for example urea/formaldehyde polymers. To effect the colour formation only within a limited temperature range substances such as urea, thiourea, diphenyl thiourea, acetamide, acetanilide, benzene sulfanilide, bis(stearoyl)ethylenediamide, stearamide, phthalic anhydride, metal stearates such as zinc stearate, phthalonitrile, dibenzyl terephthalate, dimethyl terephthalate or other appropriate fusible products which induce the simultaneous melting of the colour former and the developer may be added. Thermographic recording materials preferably contain waxes, e.g. carnauba wax, montan wax, paraffin wax, polyethylene wax, condensates of higher fatty acid amides and formaldehyde, or condensates of higher fatty acids and ethylenediamine.

A further utility of the compounds of formulae I is the formation of a coloured image by means of the photocurable microcapsules described e.g. in German Offenlegungsschrift 3 247 488.

The invention is illustrated by the following Examples in which percentages are by weight unless otherwise indicated.

In the Examples the individual substituents are numbered as follows: when A is a benzene ring, depending on the meaning of Z the invention relates to isoindolo[1,2-a]3,1-benzoxazine (Z=O) or isoindolo[1,2-a]3,1-quinazoline (Z=NR).

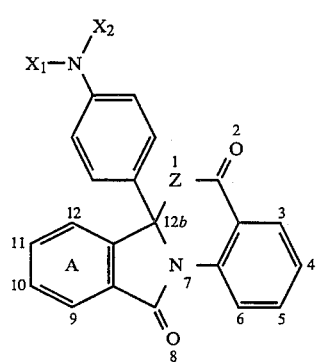

Similarly, the compounds of formula (I) are named in which the ring. A is a heteroaromatic radical or a fused benzene ring or a fused heteroaromatic radical.

EXAMPLE 1

10-Dimethylamino-12b-(4'-dimethylaminophenyl)-2,7,8,12b-tetrahydroisoindolo[1,2-a]3,1-benzoxazine-2,8-dione 18.6 parts of 4,4'-bis(dimethylamino)benzophenone-2-carboxylic acid 9.9 parts of anthranilic acid, and 0.5 part of p-toluenesulfonic acid are heated to the boil in 150 ml of chlorobenzene for 3.5 h in a water separator. After neutralisation with triethylamine and filtration of the solution over Alox, the resultant yellow solution is concentrated and the residue is dissolved in a minor amount of hot chlorobenzene. The solution is cooled and the crystallised product is isolated by filtration and dried.

Yield: 19.6 parts of the compound of formula

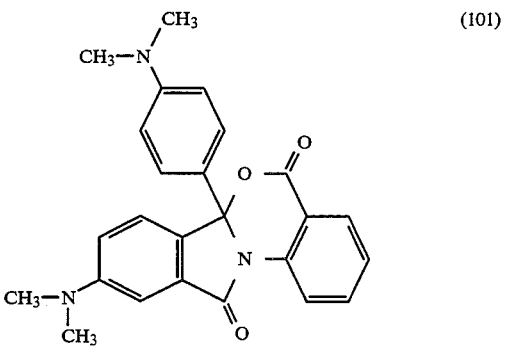

(101)

in the form of crystals.

Melting point: 227°–8° C.

A solution of this compound in toluene gives a greenish blue image when contacted with acid clay.

EXAMPLE 2

10-Dimethylamino-12b-(4'-diethylaminophenyl)-2,7,8,12b-tetrahydroisoindolo[1,2a]3,1-benzoxazine-2,8-dione 19.5 parts of 4-diethylamino-4'-dimethylamino-2'-carboxylic acid, 9.9 parts of anthranilic acid, and 0.5 part of p-toluenesulfonic acid are heated to the boil in 150 ml of chlorobenzene for 4 h in a water separator. After neutralisation with triethylamine, the solution is filtered over Alox. The resultant solution is concentrated and the residue is recrystallised from a minor amount of hot toluene, giving 17.2 pans of the compound of formula

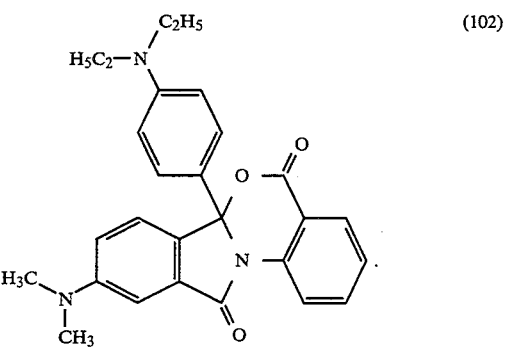

(102)

Melting point: 211°–213° C.

The compounds of Table 1 can be prepared in accordance with the general procedure described in this Example:

Compounds of formula

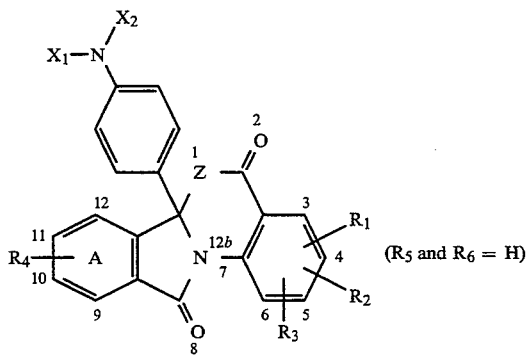

(R₅ and R₆ = H)

| Cmpd. No. | $X_1$ | $X_2$ | $R_4$ | Z | $R_1$ | $R_2$ | $R_3$ |
|---|---|---|---|---|---|---|---|
| 103 | $CH_3$ | $CH_3$ | 10-N(CH₃)₂ | O | 5-NO₂ | H | H |
| 104 | $CH_3$ | $CH_3$ | 10-N(CH₃)₂ | O | 4-I | 6-I | H |
| 105 | $C_2H_5$ | $C_2H_5$ | 10-N(CH₃)₂ | O | 4-OH | H | H |
| 106 | $CH_3$ | $CH_3$ | 10-N(CH₃)₂ | O | 6-CH₃ | H | H |
| 107 | $C_2H_5$ | $C_2H_5$ | 10-N(CH₃)₂ | O | 5-Cl | H | H |
| 108 | $C_4H_9$ | $C_4H_9$ | 10-N(C₄H₉)₂ | O | 6-Br | H | H |
| 109 | $CH_3$ | $CH_3$ | 10-N(C₂H₅) | O | 6-Cl | H | H |
| 110 | $CH_3$ | $CH_3$ | 10-N(CH₃)₂ | O | 6-I | H | H |
| 111 | $C_2H_5$ | $C_2H_5$ | 10-N(C₂H₅)₂ | O | 6-OH | H | H |
| 112 | $CH_3$ | $CH_3$ | 10-N(CH₃)₂ | O | 6-CH₃ | H | H |
| 113 | $CH_3$ | $CH_3$ | 10-N(CH₃)₂ | O | 4-CH₃O | 5-CH₃O | |
| 114 | $C_3H_7$ | $C_3H_7$ | 10-N(CH₃)₂ | O | 6-CH₃O | H | H |
| 115 | $CH_3$ | $CH_3$ | 10-N(CH₃)₂ | O | 6-NO₂ | H | H |
| 116 | $CH_3$ | $CH_3$ | 10-N(C₃H₇)₂ | O | 4-Cl | 6-Cl | H |
| 117 | $CH_3$ | $CH_3$ | 10-N(CH₃)₂ | O | 4-CH₃ | 6-CH₃ | H |
| 118 | $C_4H_9$ | $C_4H_9$ | 10-N(CH₃)₂ | O | 4-(O—CH₂O)-5 | | H |
| 119 | $CH_3$ | $CH_3$ | 10-N(C₄H₉)₂ | O | 4-NO₂ | H | H |
| 120 | $CH_3$ | $CH_3$ | 10-N(CH₃)₂ | O | 4-SO₃H | H | H |
| 121 | $CH_3$ | $CH_3$ | 10-N(CH₃)₂ | O | 4-CH₃ | 5-CH₃ | 6-CH₃ |
| 122 | $CH_3$ | $CH_3$ | 10-N(CH₃)₂ | O | 6-F | H | H |
| 123 | —(CH₂)₅— | | 10-N(C₂H₅)₂ | O | 6-CH₃ | H | H |
| Verb No. | | | | | | | |
| 124 | —(CH₂)₅— | —(CH₂)₅— | | O | 6-CH₃ | H | H |
| 125 | $C_2H_5$ | $C_2H_5$ | 10-OC₂H₅ | O | H | H | H |

The $\lambda_{max}$ values of the compounds of the Table can be determined when they are applied to acid clay. The values are in the range from 500 to 550 nm (measured in remission).

USE EXAMPLES

USE EXAMPLE 1

Preparation of a Pressure-sensitive Copying Paper

A solution of 3 g of the lactam (101) of Example 1 in 80 g of diisopropylnaphthalene and 17 g of kerosene is microencapsulated by coacervation in per se known manner with gelatin and carboxymethyl cellulose. The microcapsules are mixed with starch solution and coated on a sheet of paper. The face of a second sheet of paper is coated with activated clay as colour developer. The first sheet containing the colour former and the paper coated with the developer are laid over each other with the coated sides face to face. Pressure is exerted on the first sheet by writing by hand or typewriter and a deep blue image of excellent lightfastness develops on the sheet coated with the developer.

USE EXAMPLE 2

Preparation of a Pressure-sensitive Copying Paper 1 g of the lactam (101) of Example 1 is dissolved in 17 g of toluene. With stirring, 12 g of polyvinyl acetate, 8 g of calcium carbonate and 2 g of titanium dioxide are added to this solution. The resultant suspension is diluted with toluene in the weight ratio of 1:1 and coated with a 10 μm doctor knife onto a sheet of paper. On this sheet of paper is laid a second sheet of paper, the underside of which has been coated to a weight of 3 g/m² with a mixture comprising 1 part of an amide wax, 1 part of a stearin wax and 1 part of zinc chloride. Pressure is exerted on the top sheet by writing by hand or typewriter and a deep lightfast blue image develops on the sheet coated with the colour former.

What is claimed is:

1. A lactam of formula I

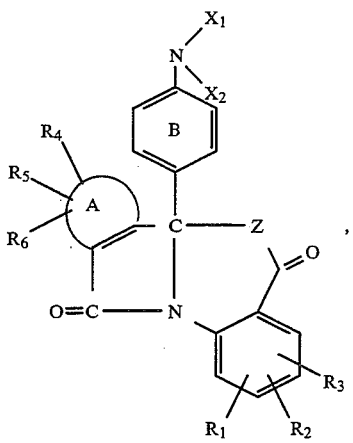

(I)

wherein
- the ring A is benzene, naphthalene, quinoline, quinoxaline or a nitrogen containing heterocycle which is aromatic and contains 6 ring atoms;
- the ring B is a benzene nucleus which may be substituted by halogen, lower alkyl, lower alkoxy, benzyloxy, or lower alkylcarbonylamino, mono- or di-lower alkylamino;
- Z is O;
- R is hydrogen; lower alkyl which is unsubstituted or substituted by halogen, hydroxy, cyano, benzoyl, acyl, di-lower alkylamino or lower alkoxy; cycloalkyl of 5 to 10 carbon atoms; aryl or aralkyl which are each unsubstituted or ring-substituted by halogen, cyano, nitro, $C_1$–$C_4$haloalkyl, lower alkyl, lower alkoxy, lower alkoxycarbonyl or acyl; acyl; N-lower alkylcarbamoyl; or unsubstituted or ring-substituted N-arylcarbamoyl;
- $R_1$, $R_2$ and $R_3$ are each independently of one another hydrogen; lower alkyl; lower alkoxy; lower alkylthio; lower alkylsulfonyl; sulfo; hydroxy; nitro; halogen; amino; mono-lower alkylamino; di-lower alkylamino; arylamino; aryl-lower alkylamino; diarylamino; aralkylamino; aralkyl-lower alkylamino; diaralkylamino; or a wholly or partially saturated heterocyclic radical which is attached at a ring nitrogen atom;
- $R_2$ and $R_3$ together are an unsubstituted or a lower alkyl-substituted, vicinally linked methylenedioxy or 1,2-ethylene dioxy group;
- $R_4$, $R_5$ and $R_6$ are each independently of one another hydrogen; halogen; cyano; nitro; lower alkyl; lower alkylthio; lower alkylcarbonyl; lower alkoxycarbonyl; amino; mono-lower alkylamino; di-lower alkylamino; arylamino; aryl-lower alkylamino; diarylamino, aralkylamino; aralkyl-lower alkylamino; diaralkylamino; cycloalkylamino; dicycloalkylamino; lower alkyl-cycloalkylamino; lower alkoxy; lower alkylsulfonyl; or a wholly or partially saturated heterocyclic radical which is attached at a ring nitrogen atom;
- $X_1$ and $X_2$ are each independently of the other hydrogen; alkyl of not more than 12 carbon atoms which is unsubstituted or substituted by halogen, hydroxy, cyano, tetrahydrofuryl or lower alkoxy; acyl of 1 to 8 carbon atoms; cycloalkyl of 5 to 10 carbon atoms; or aralkyl or aryl which are each unsubstituted or ring-substituted by halogen, cyano, nitro, trifluoromethyl, lower alkyl, lower alkoxy, lower alkoxycarbonyl, —NX'X" or 4-X'X"N- phenylamino, wherein X' and X" are each independently of the other hydrogen, lower alkyl, cyclohexyl, benzyl or phenyl; or
- $X_1$ and $X_2$ together with the linking nitrogen atom are a 5- or 6-membered, saturated, heterocyclic radical.

2. A compound according to claim 1 of formula I

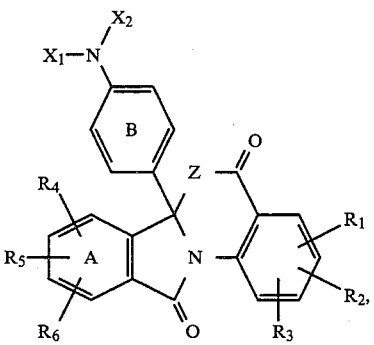

(I)

wherein
- the ring B is a benzene nucleus which may be substituted by halogen, lower alkyl, lower alkoxy or benzyloxy;
- Z is, or O;
- R is hydrogen, lower alkyl which is unsubstituted or substituted by halogen or lower alkoxy; cycloalkyl of 5 to 10 carbon atoms; phenyl or benzyl which are each unsubstituted or ring-substituted by halogen, cyano, nitro, $C_1$–$C_4$haloalkyl, lower alkyl or lower alkoxy; acyl;
- $R_1$, $R_2$ and $R_3$ are each independently of one another hydrogen; lower alkyl; lower alkoxy; lower alkylthio; lower alkylsulfonyl; sulfo; hydroxy; nitro; halogen; amino; mono-lower alkylamino; di-lower alkylamino; arylamino; aryl-lower alkylamino; diarylamino; aralkylamino; aralkyl-lower alkylamino; diaralkylamino; or a wholly or partially saturated heterocyclic radical which is attached at a ring nitrogen atom;
- $R_2$ and $R_3$ together are an unsubstituted or a lower alkyl-substituted, vicinally linked methylenedioxy or 1,2-ethylene dioxy group;
- $R_4$, $R_5$ and $R_6$ are each independently of one another hydrogen; halogen; cyano; nitro; lower alkyl; lower alkylthio; lower alkylcarbonyl; lower alkoxycarbonyl; amino; mono-lower alkylamino; di-lower alkylamino; arylamino; aryl-lower alkylamino; diarylamino, aralkylamino; aralkyl-lower alkylamino; diaralkylamino; cycloalkylamino; dicycloalkylamino; lower alkyl-cycloalkylamino; lower alkoxy; lower alkylsulfonyl; or a wholly or partially saturated heterocyclic radical which is attached at a ring nitrogen atom;
- $X_1$ and $X_2$ are each independently of the other hydrogen; alkyl of not more than 12 carbon atoms which is unsubstituted or substituted by halogen, hydroxy, cyano, tetrahydrofuryl or lower alkoxy; acyl of 1 to 8 carbon atoms; cycloalkyl of 5 to 10 carbon atoms; or aralkyl or aryl which are each unsubstituted or ring-substituted by halogen, cyano, nitro, trifluoromethyl, lower alkyl, lower alkoxy; or $X_1$ and $X_2$ together with the linking nitrogen atom are a 5- or 6-membered, saturated, heterocyclic radical.

3. A compound according to claim 1 of formula I (I)

wherein the ring B is a benzene nucleus which is unsubstituted or substituted by halogen or lower alkyl;

Z is, or O;

is hydrogen;

$R_1$ is hydrogen; $C_1$-$C_4$alkyl; $C_1$-$C_4$alkoxy; sulfo; nitro; halogen; mono-$C_1$-$C_4$alkylamino; di-$C_1$-$C_4$alkylamino; phenylamino; phenyl-$C_1$-$C_4$alkylamino; diphenylamino; benzylamino; benzyl-$C_1$-$C_4$alkylamino; dibenzylamino;

$R_2$ and $R_3$ are each independently of the other hydrogen, $C_1$-$C_4$alkyl; or halogen;

$R_2$ and $R_3$ together are a vicinally linked methylenedioxy or 1,2-ethylene dioxy group;

$R_4$ is hydrogen; amino; mono-$C_1$-$C_4$alkylamino; di-$C_1$-$C_4$alkylamino; phenylamino; phenyl-$C_1$-$C_4$alkylamino; diphenylamino; benzylamino; benzyl-$C_1$-$C_4$alkylamino; dibenzylamino; cycloalkylamino; dicycloalkylamino; or $C_1$-$C_4$alkylcycloalkylamino;

$R_5$ and $R_6$ are each independently of the other hydrogen; halogen; cyano; nitro; $C_1$-$C_4$alkyl; $C_1$-$C_4$alkylthio; or $C_1$-$C_4$alkoxy;

$X_1$ and $X_2$ are each independently of the other hydrogen; unsubstituted or $C_1$-$C_4$alkoxy-substituted alkyl of not more than 12 carbon atoms; cyclohexyl; benzyl or phenyl which are each unsubstituted or ting-substituted by halogen, $C_1$-$C_4$alkyl or $C_1$-$C_4$alkoxy; or $X_1$ and $X_2$ together with the linking nitrogen atom are a 5- or 6-membered, saturated, heterocyclic radical.

4. A compound of formula I according to claim 1, wherein $R_1$ is as previously defined, $R_2$ is hydrogen, halogen or $C_1$-$C_4$alkyl, and $R_3$ is halogen or hydrogen.

5. A compound of formula I according to claim 1, wherein $R_1$ is mono-$C_1$-$C_4$alkylamino or di-$C_1$-$C_4$alkylamino, $R_2$ is hydrogen or $C_1$-$C_4$alkyl, and $R_3$ is hydrogen.

6. A compound of formula I according to claim 1, wherein $R_4$ is $C_1$-$C_4$alkoxy, mono-$C_1$-$C_4$alkylamino, di-$C_1$-$C_4$alkylamino, phenylamino, phenyl-$C_1$-$C_4$alkylamino, diphenylamino, benzylamino, benzyl-$C_1$-$C_4$alkylamino, dibenzylamino, cycloalkylamino, dicycloalkylamino, or $C_1$-$C_4$alkylcycloalkylamino.

7. A compound of formula I according to claim 1, wherein $R_4$ is mono-$C_1$-$C_4$alkylamino, di-$C_1$-$C_4$alkylamino, phenylamino, phenyl-$C_1$-$C_4$alkylamino, diphenylamino, benzylamino, benzyl-$C_1$-$C_4$alkylamino or dibenzylamino.

8. A compound of formula I according to claim 1, wherein $X_1$ and $X_2$ are each independently of the other hydrogen, unsubstituted alkyl of not more than 6 carbon atoms, benzyl or phenyl.

9. A compound of formula I according to claim 1, wherein $X_1$ and $X_2$ are each independently of the other unsubstituted alkyl of not more than 6 carbon atoms, benzyl or phenyl.

10. A lactam of claim 1 wherein $X_1$ and $X_2$ are each independently $C_1$-$C_4$alkyl, $R_4$ is —N—($C_1$-$C_4$alkyl)$_2$.

11. A lactam of claim 10 wherein $R_5$ and $R_6$ are hydrogen.

12. A lactam of claim 10 wherein $R_4$ is on the 10-position of ring A.

13. A lactam of claim 11 wherein $R_4$ is on the 10-position of ring A.

* * * * *